(12) United States Patent
Yamamoto

(10) Patent No.: US 10,180,425 B2
(45) Date of Patent: Jan. 15, 2019

(54) SPFS BIOSENSOR BASED ON NUCLEIC ACID LIGAND STRUCTURAL CHANGE

(71) Applicant: KONICA MINOLTA LABORATORY U.S.A., INC., San Mateo, CA (US)

(72) Inventor: Noriaki Yamamoto, Tokyo (JP)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 0 days.

(21) Appl. No.: 15/504,004

(22) PCT Filed: Sep. 1, 2015

(86) PCT No.: PCT/US2015/047988
§ 371 (c)(1),
(2) Date: Feb. 14, 2017

(87) PCT Pub. No.: WO2016/040059
PCT Pub. Date: Mar. 17, 2016

(65) Prior Publication Data
US 2017/0241993 A1    Aug. 24, 2017

Related U.S. Application Data

(60) Provisional application No. 62/048,488, filed on Sep. 10, 2014.

(51) Int. Cl.
| | | |
|---|---|---|
| G01N 33/542 | (2006.01) | |
| G01N 21/64 | (2006.01) | |
| C12Q 1/6804 | (2018.01) | |
| G01N 33/543 | (2006.01) | |

(52) U.S. Cl.
CPC ......... *G01N 33/542* (2013.01); *C12Q 1/6804* (2013.01); *G01N 21/648* (2013.01); *G01N 21/6428* (2013.01); *G01N 33/54373* (2013.01); *G01N 2021/6417* (2013.01); *G01N 2021/6439* (2013.01)

(58) Field of Classification Search
CPC ...... C12Q 1/68; C12Q 1/6804; G01N 33/542; G01N 21/648
See application file for complete search history.

(56) References Cited

U.S. PATENT DOCUMENTS

| | | | | |
|---|---|---|---|---|
| 8,107,071 B2 * | 1/2012 | Kimura | .............. | G01N 21/6428 356/318 |
| 2002/0039738 A1 | 4/2002 | Williams et al. | | |
| 2008/0014581 A1 | 1/2008 | Nakahara et al. | | |
| 2008/0037022 A1 | 2/2008 | Nishikawa et al. | | |
| 2009/0137418 A1 * | 5/2009 | Miller | .................. | B01J 19/0046 506/9 |
| 2009/0264308 A1 | 10/2009 | Broer et al. | | |
| 2010/0068824 A1 * | 3/2010 | Kimura | ................ | G01N 21/648 436/501 |
| 2012/0196385 A1 | 8/2012 | Yamamoto et al. | | |

FOREIGN PATENT DOCUMENTS

JP    2009-250960 A    10/2009

OTHER PUBLICATIONS

Cao et al, Electric Field Assisted Surface Plasmon-Coupled Directional Emission: An Active Strategy on Enhancing Sensitivity for DNA Sensing and Efficient Discrimination of Single Base Mutation, 2011, J. Am. Chem. Soc., 133, 1787-1789 (Year: 2011).*
Cao et al, Electric Field Assisted Surface Plasmon-Coupled Directional Emission: An Active Strategy on Enhancing Sensitivity for DNA Sensing and Efficient Discrimination of Single Base Mutation, 2011, J. Am. Chem. Soc., 133, 1787-1789- supplemental information (Year: 2011).*
International Search Report in the parent PCT application No. PCT/US2015/047988, dated Nov. 23, 2015.
Written Opinion in the parent PCT application No. PCT/US2015/047988, dated Nov. 23, 2015.
Liebermann et al., "Surface-plasmon field-enhanced fluorescence spectroscopy", Colloids and Surfaces A: Physicochemical Engineering Aspects, 2000, 171, pp. 115-130.
Knoir et al., "Principles and Applications of Surface Plasmon Field-Enhanced Fluorescence Techniques", Topics in Fluorescence Spectroscopy, vol. 8: Radiative Decay Engineering, Edited by Geddes and Lakowicz, Springer Science+Business Media, Inc., New York, 2005, pp. 305-332.
Vallee-Belisle et al., "Bio-electrochemical switches for the quantitative detection of antibodies directly in whole blood", J Am Chem Soc., Sep. 19, 2012, 134(37).
Japanese Office Action, dated Aug. 21, 2018 in a counterpart Japanese patent application, No. JP 2017-513481.

* cited by examiner

*Primary Examiner* — Narayan K Bhat
(74) *Attorney, Agent, or Firm* — Chen Yoshimura LLP

(57) ABSTRACT

A DNA ligand capable of structural changes upon binding to a target is used as a molecular switch with a SPFS (surface plasmon field-enhanced fluorescence spectroscopy) biosensor to realize one-step SPFS biosensing with rapid turnaround time. The SPFS biosensor has a thin metal film on a prism; when a light of a certain wavelength irradiates on the prism at a certain angle, a strong electrical field is generated at the surface of the metal film. The DNA is immobilized on the metal film surface with its free terminal modified with a fluorescent marker. Without the target, the DNA is folded and the fluorescent marker is located in the region of metal quenching near the metal surface. Upon binding to the target, the DNA is extended and the fluorescent marker is located in the region of enhanced electric field near the metal surface and emits a strong fluorescent signal.

4 Claims, 10 Drawing Sheets

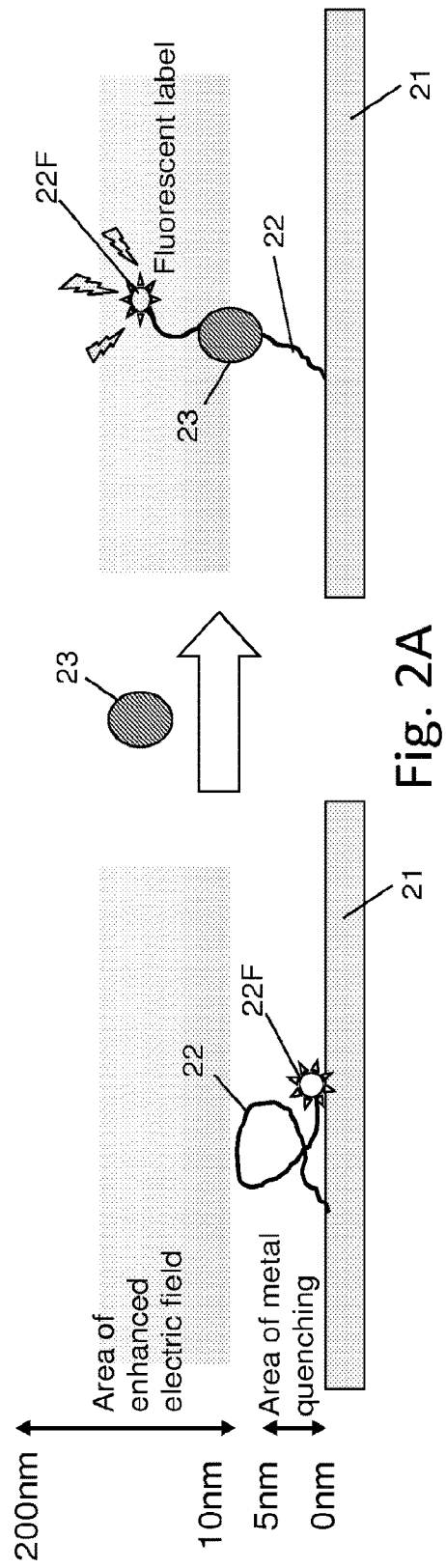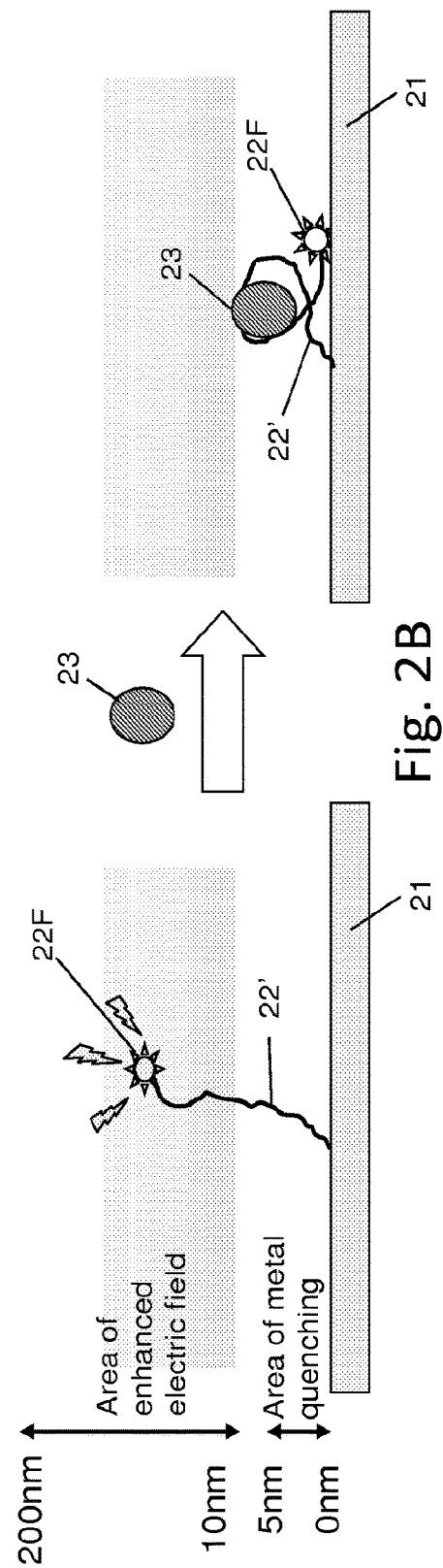

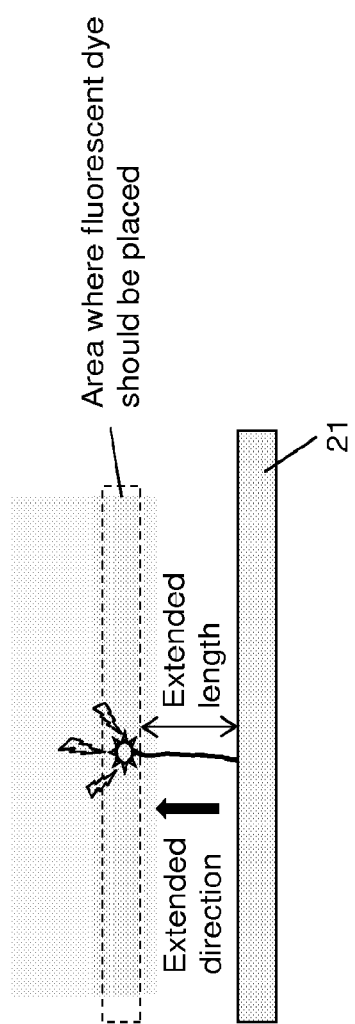

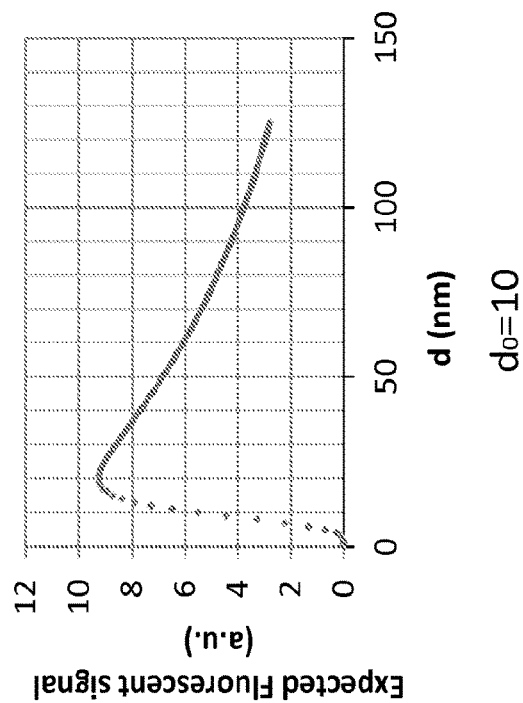
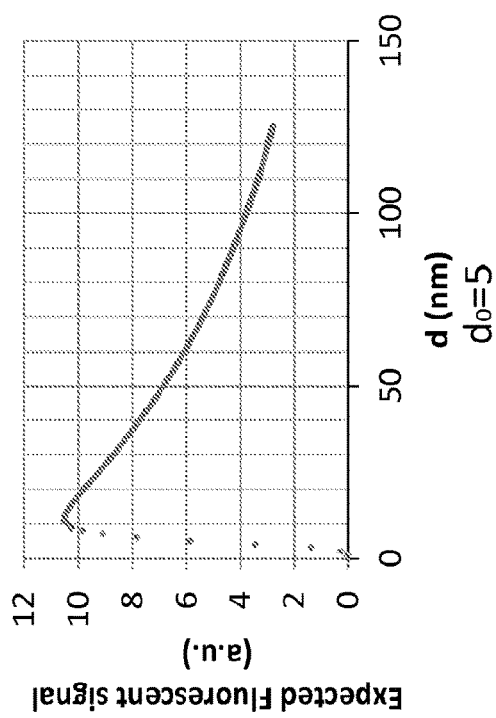
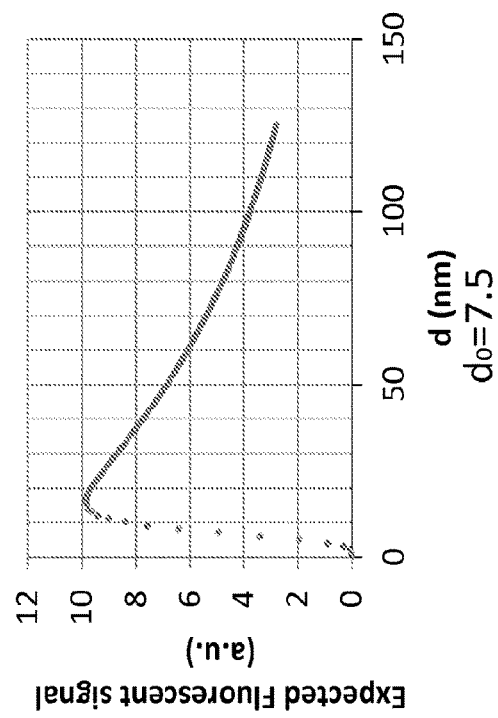
Fig. 4

SPFS BIOSENSOR BASED ON NUCLEIC ACID LIGAND STRUCTURAL CHANGE

BACKGROUND OF THE INVENTION

Field of the Invention

This invention relates to surface plasmon field-enhanced fluorescence spectroscopy (SPFS), and in particular, it relates to SPFS biosensors based on nucleic acid ligand structural change.

Description of Related Art

Surface plasmon field-enhanced fluorescence spectroscopy (SPFS) is a known biosensing technology. The technology is described in, for example, T. Liebermann, W. Knoll, Surface-plasmon field-enhanced fluorescence spectroscopy, Colloids and Surfaces A: Physicochem. Eng. Aspects 171 (2000) 115-130 ("Liebermann 2000"); and Wolfgang Knoir, Fang Yu, Thomas Neumann, Lifang Niu, and Evelyne L. Schmid, Principles And Applications Of Surface Plasmon Field-Enhanced Fluorescence Techniques, in Topics in Fluorescence Spectroscopy, Volume 8: Radiative Decay Engineering, Edited by Geddes and Lakowicz, Springer Science+Business Media, Inc., New York, 2005, p. 305-332. These references show the principle and setup of SPFS biosensors in general. SPFS offers high-sensitivity detection through advanced sensing technology.

FIG. 1A, taken from FIG. 5 of the Liebermann 2000 paper, illustrates the setup of an SPFS system. FIG. 1B, taken from FIG. 6(a) of the same paper, illustrates the structure of the prism and flow cell used in the SPFS system. The basic concept of SPFS is described below with reference to FIGS. 1, 1A and 1B. An SPFS biosensor includes a thin metal film on a glass or plastic prism. The metal may be, for example, gold, silver, aluminum, etc. A capture molecule is immobilized on the surface of the metal film. A biological sample is applied on the metal film. When an incident light of a certain wavelength is irradiated on the prism at a certain angle, a relatively strong electrical field is generated at the surface of the metal film. Because of quenching from the metal film, the best place for fluorescence excitation is in the region about a couple of tens to hundreds nm above the surface. In a typical device, the quenching region is within about 0-5 nm from the metal surface, and the enhanced region is about 10-200 nm from the surface. If a fluorescent label is trapped in this enhanced region, a relatively strong fluorescent signal is generated.

SPFS biosensors are based on fluorescence detection. In conventional SPFS biosensors, in addition to first antibodies that are immobilized on the thin metal film, fluorescent labeled second antibodies are generally used for protein detection. This is schematically illustrated in FIG. 1. The first antibodies 15 are immobilized on the thin metal film 11 on the prism 12. The target 17 (i.e. substance to be detected, such as protein) are added to the biosensor and captured on the immobilized first antibodies 15. Then, the fluorescent labeled second antibodies 16 are added to the biosensor and they bind to the target 17. The first antibody 15, the target 17 and the second antibody 16 form a structure such that the fluorescent label 16F on the second antibody is located in the region of enhanced electric field above the thin metal film 11, and a relatively strong fluorescent signal is generated. For unbound second antibodies or those that form non-specific binding, their fluorescent labels tend to be located outside of the enhanced region, in the metal quenching region or farther away from the surface, so they are not excited. The biosensor can be washed before the detection result is obtained. These multiple steps make the biosensor more complicated to use and the turnaround time long.

SUMMARY

Embodiments of the present invention use a DNA ligand, whose structure changes in the presence of a target, as a molecular switch on the SPFS biosensor to realize one-step SPFS biosensing with rapid turnaround time. In this biosensing method, the location of the fluorescent marker immobilized on the DNA ligand is changed from the quenching region of the SPFS biosensor to the enhanced region or vice versa, by the structural change triggered by the target.

An object of the present invention is to reduce the turnaround time and complexity of the SPFS biosensor by decreasing the number of assay steps. As a result of the combination of DNA nanoswitch technology and SPFS, high sensitivity, rapid turnaround time and simplicity of the system can be achieved.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides an optical biosensor which includes: a prism; a thin metal film formed on the prism, being configured to generate an electrical field near its surface when an incident light of a predetermined wavelength is irradiated on the prism at a predetermined angle, the electrical field forming a fluorescent quenching region adjacent the surface of the metal film and a fluorescent enhancing region located farther away from the surface than the fluorescent quenching region; and nucleic acid molecules having one end immobilized on the surface of the metal film and having another end modified with a fluorescent marker, wherein the nucleic acid molecule changes its structure either from a folded state to an extended state upon binding to a target, or from an extended state to a folded state upon binding to a target, and wherein when the nucleic acid molecule is in the extended state, the fluorescent marker is located in the fluorescent enhancing region and emits a first fluorescent signal, and when the nucleic acid molecule is in the folded state, the fluorescent marker is located in the fluorescent quenching region and emits no fluorescent signal or a second fluorescent signal which is weaker than the first fluorescent signal.

In another aspect, the present invention provides a method of using the above optical biosensor, which includes: applying a sample to the surface of the metal film of the biosensor; and measuring fluorescent signals from the biosensor.

It is to be understood that both the foregoing general description and the following detailed description are exemplary and explanatory and are intended to provide further explanation of the invention as claimed.

BRIEF DESCRIPTION OF THE DRAWINGS

FIGS. 2A and 2B schematically illustrate the principle of a SPFS biosensor using DNA molecular switches according to embodiments of the present invention.

FIG. 3 schematically illustrates an extended DNA ligand with a fluorescent label where the fluorescent label is located in the region of enhanced electrical field.

FIG. 4 illustrates exemplary fluorescent signal intensity vs. distance curves for various Forster distances.

DETAILED DESCRIPTION OF PREFERRED EMBODIMENTS

Embodiments of the present invention use a DNA ligand whose structure changes in the presence of the target as a molecular switch (also referred to as the DNA nanoswitch) in an SPFS sensor. This technology effectively uses DNA structural change in the SPFS biosensor's quenching region and enhanced region to realize a one-step assay.

FIG. 2A schematically illustrates the basic concept of using the DNA molecular switch in SPFS according to an embodiment of the present invention. The molecular switch employs a DNA molecule 22, one end of which is immobilized on the metal surface 21 of the sensor, the other end of which is modified with a fluorescent dye 22F. In the absence of the target 23 (which may be, for example, a protein molecule or other biological molecules or agents), the DNA molecule 22 is folded and the fluorescent dye 22F is located near the metal surface 21, in the region of metal quenching, and is quenched (see the left hand side of FIG. 2A). In the presence of the target 23, the DNA structure 22 is changed into an extended shape, and the fluorescent dye 22F is now located in the region of enhanced electrical field and emits a relatively strong fluorescent signal (see the right hand side of FIG. 2A).

Figure 1:
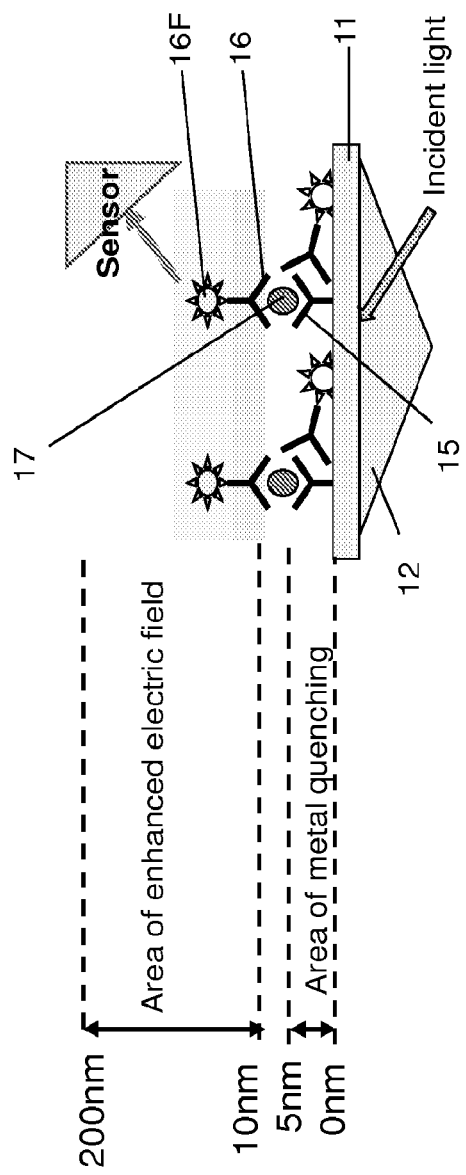
FIGS. 1, 1A and 1B schematically illustrate the principle and setup of a conventional SPFS biosensor.
Figure 1A:
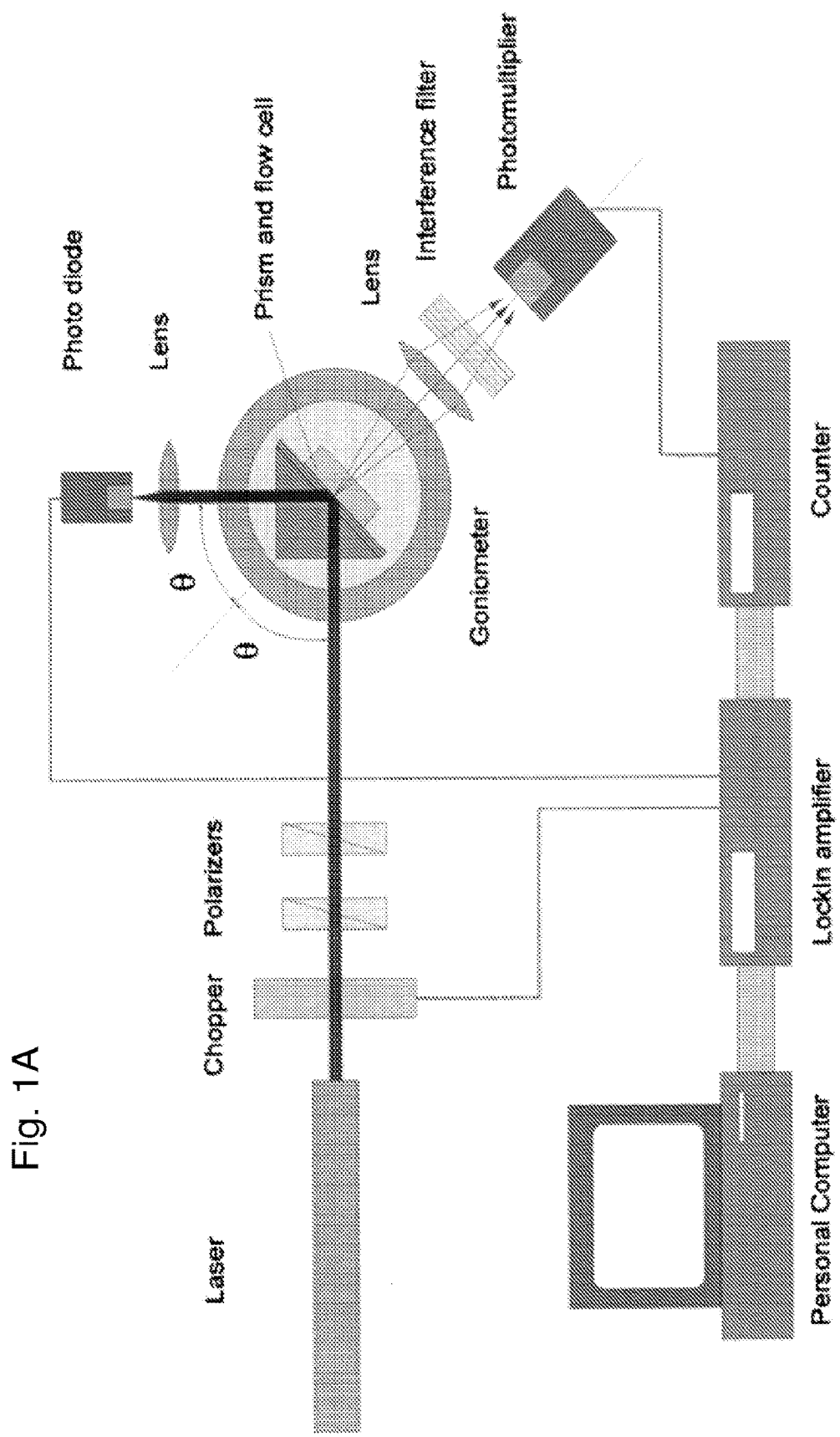
Figure 1B:
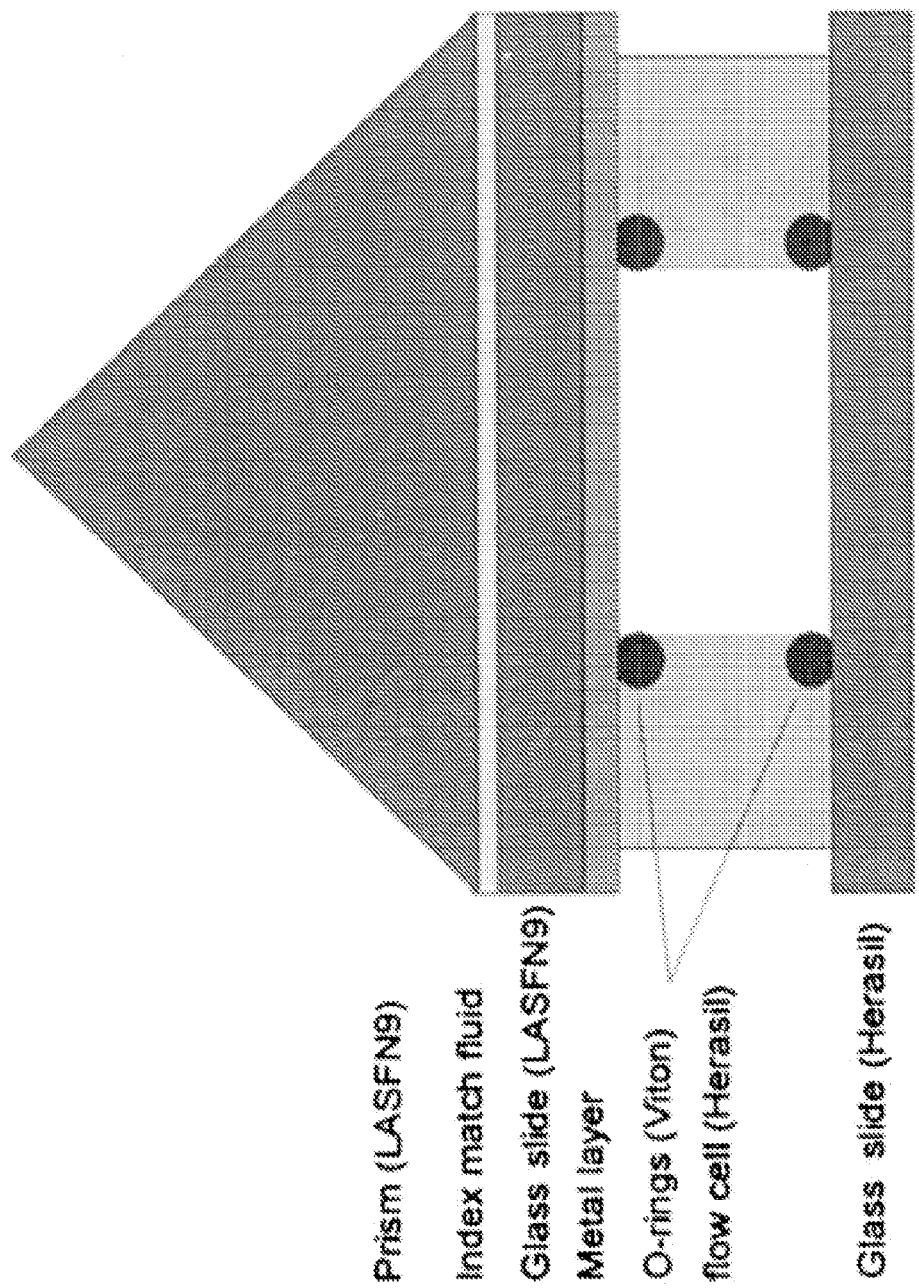

FIG. 2B schematically illustrates an alternative DNA molecular switch which can be used with SPFS according to another embodiment of the present invention, where the DNA molecule 22' is unfolded in the absence of the target 23 so the fluorescent dye 22F at the other end of the DNA emits a relatively strong signal, but is folded in the presence of target so the fluorescent dye is quenched. This biosensor is otherwise similar to that shown in FIG. 2A. The prism of the biosensor is not shown in FIGS. 2A and 2B, but it is located below the thin metal film 21 in a configuration similar to that shown in FIG. 1.

To use this biosensor, only one step of applying the sample containing the target is required, before the fluorescent signal can be measured.

As described in the Liebermann 2000 paper, the highest fluorescent signal is obtained at locations at a short distance from the metal surface. Based on the information described in that paper (for example, FIG. 3 of the paper and related description therein), for the example given in that paper, the optimum height for fluorescence signal is preferably 10-100 nm, more preferably 10-30 nm, from the surface. Thus, in order to achieve a high signal-to-noise ratio of the fluorescent signal, it is important that in the presence (in the example of FIG. 2A; or absence in the example of FIG. 2B) of the target, the fluorescent dye is located at where the fluorescent signal is expected to be the highest, and in the absence (or presence) of the target, it is located at where the fluorescent signal is expected to be the lowest. Under the above example, the dye should be within the space of less than 5 nm height from the surface in the absence of the target, preferably as close to the surface as practical; and when the DNA ligand binds to the target, the dye should be at the location where the fluorescent signal is close the maximum, e.g., 10-100 nm, more preferably 10-30 nm, from the metal surface. To achieve that, the length of the DNA ligand and the direction of the DNA ligand extension (in the presence or absence of the target) are important, as illustrated in FIG. 3.

The optimum distance of the fluorescence intensity curve is dependent on the Forster distance or radius ($d_0$) of the fluorescence quenching. The Forster radius $d_0$ is determined by the types of donor and acceptor, the wavelength of the fluorescent light, and the refractive index of the medium. Thus, $d_0$ can be adjusted by the selection of the donor and/or acceptor materials, and/or factors that affect the refractive index of the medium, such as additives, temperature etc. Typical values of $d_0$ are in the range of 5-10 nm. FIG. 4 shows three fluorescence intensity curves for different $d_0$ values. Thus, the optimum DNA ligand length for the SPFS biosensor is dependent on the $d_0$ value; in most cases, the optimum length should be about 10-30 nm.

Figure 5:
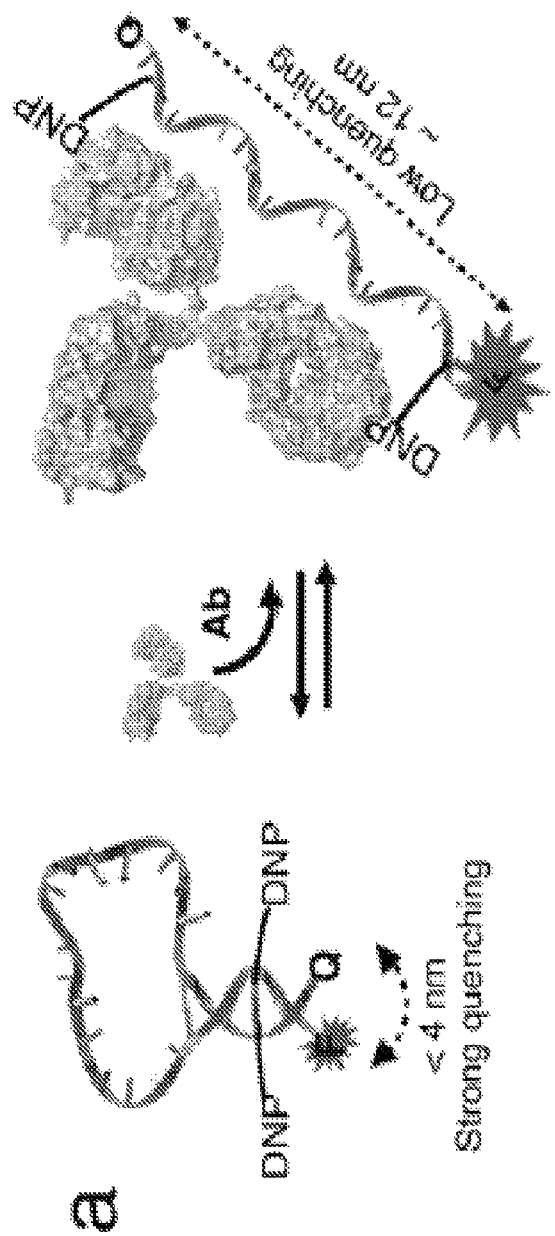
FIG. 5 illustrates an exemplary DNA molecule that can be used as the molecular switch in embodiments of the present invention.

One DNA ligand that can act as a DNA molecular switch is described in Vallee-Belisle et al. J Am Chem Soc. 2012, September 19, 134(37) ("Vallee-Belisle 2012"), shown in see FIG. 5, which is reproduced from this paper. In the DNA molecule described in this paper, one terminus of the DNA is modified with a fluorescent marker (fluorescent dye) "F", and the other terminus is modified with a quenching module "Q". When the DNA is folded in the absence of the target (an antibody), the fluorescent dye F and the quenching module Q are located in close proximity of each other, and the fluorescence is quenched. When the DNA is unfolded in the presence of the target, the fluorescent dye F is no longer quenched by the quenching module Q. The originally folded part of this DNA ligand is extended to 12 nm in length upon binding of the target.

This DNA may be adapted for use in the SPFS biosensors according to embodiments of the present invention. The end of the DNA that does not have the fluorescent dye F is immobilized on the metal film of the SPFS sensor. The quenching module Q is not required, as the fluorescence of the dye will be quenched by the thin metal film when the DNA is folded. However, the quenching module Q can be optionally provided as it further reduces the fluorescent signal in the folded state.

Figure 6C:
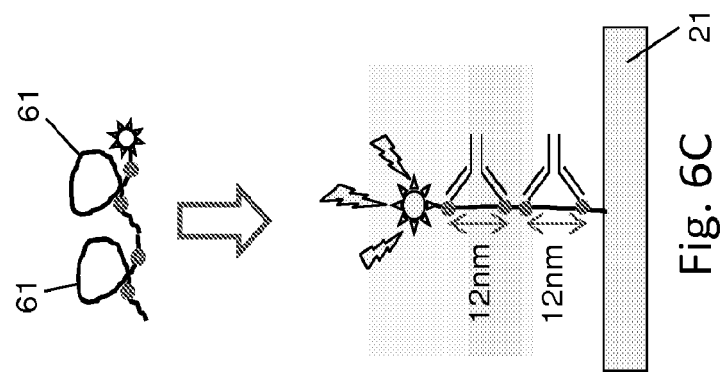
FIGS. 6A-6C schematically illustrate examples of DNA ligands with and without length extension which can be used as the molecular switch in embodiments of the present invention.
Figure 6B:
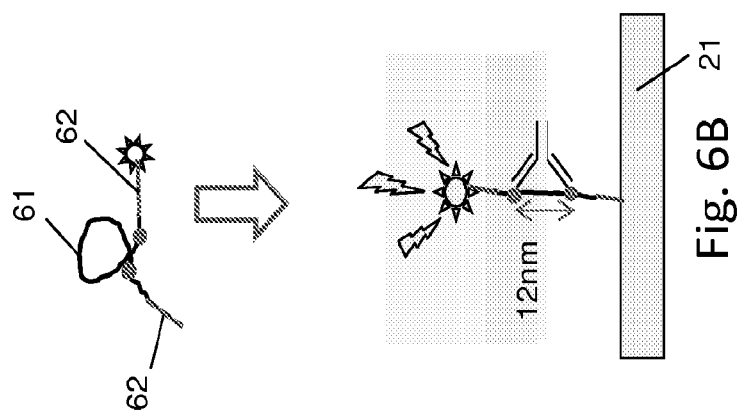
Figure 6A:
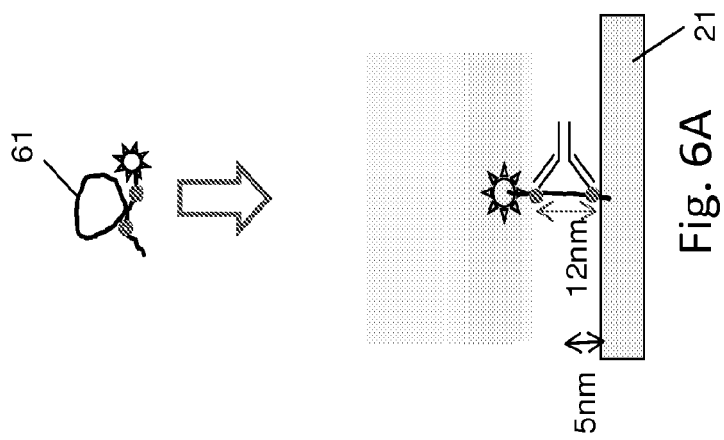

Since the optimum region for fluorescence in the SPFS sensor depends on the Forster radius ($d_0$), if the length of the extended DNA is not long enough to place the fluorescent dye in this region, additional DNA sequences can be added to place the fluorescent dye at the optimum position, which is within 10-30 nm from the metal surface 21. If $d_0=5$, the position with the highest fluorescent signal will be about 10 nm (see FIG. 4), so the DNA ligand 61 described in the Vallee-Belisle et al. 2012 paper can be used without any modification (see FIG. 6A). On the other hand, if $d_0=10$, the position with the highest fluorescent signal will be about 20 nm; in this case, the length of this DNA ligand needs to be extended so that the fluorescent label will be located in the regions of highest fluorescent signal when the DNA ligand is unfolded. For example, additional DNA sequences 62 can be added to this DNA ligand 61 at both terminus of the folded part, and the fluorescent dye and the immobilization site are at the distal ends of the extended DNA (see FIG. 6B), or multiple DNA molecules 61 can be joined and aligned in a tandem manner to extend the length (see FIG. 6C). In FIG. 6C, two antibodies (targets) are shown as binding to the tandem DNA ligand.

Figure 7:
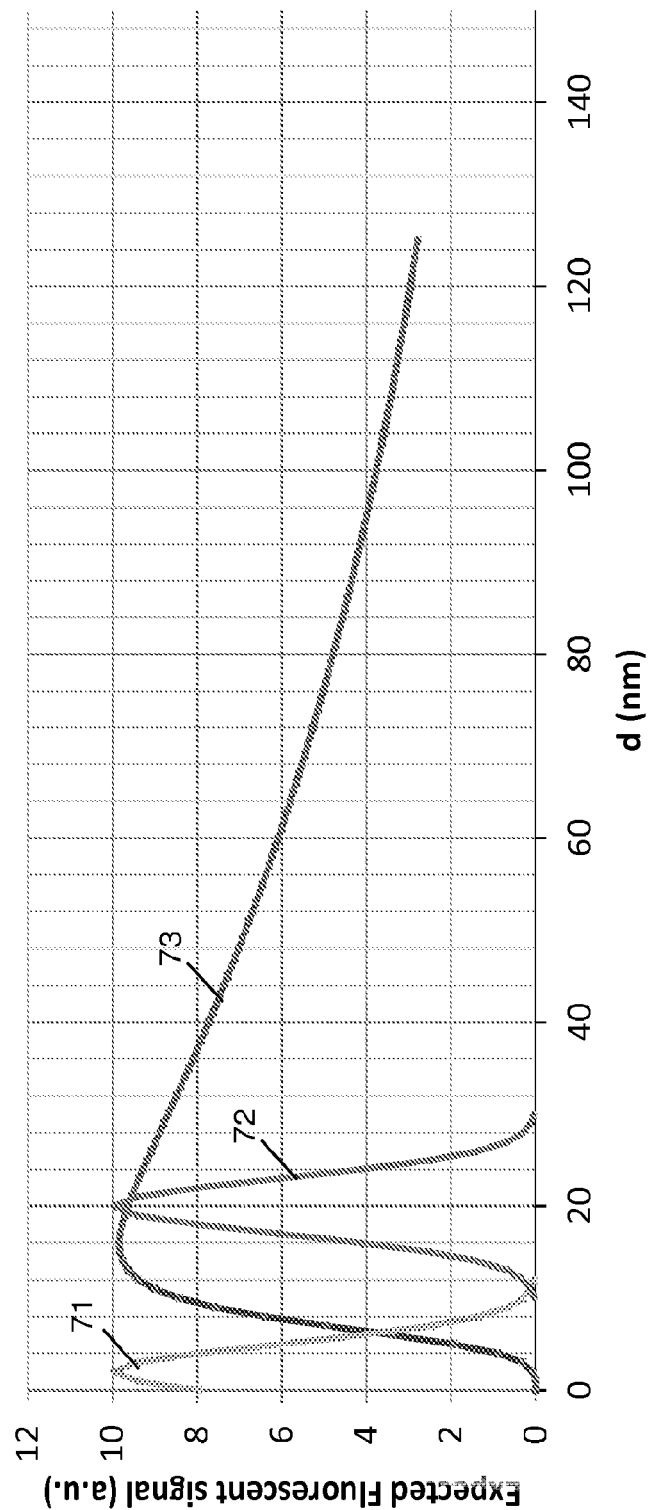
FIG. 7 shows position distribution curves of the fluorescent dye on the DNA ligand with and without the target.

The position of the fluorescent dye in the sample tends to have a distribution, due to the fact that the extended DNA molecules are not always fully extended and perpendicular to the surface of the film. The DNA switch should be chosen or adjusted to have a position distribution which gives the highest fluorescent signal when the target is present, and a position distribution which gives the lowest fluorescent signal when the target is absent. In FIG. 7, the curve 71 illustrates an exemplary fluorescent dye position distribution when the target is absent (g(d)), the curve 72 illustrates an exemplary fluorescent dye position distribution when the target is present (h(d)), and the curve 73 illustrates an exemplary fluorescent signal intensity as a function of distance (f(d)). The signal intensity from the sample is the product of the position distribution and the fluorescent intensity:

Signal=∫f(d)*h(d)dd

Noise=∫f(d)*g(d)dd

If the extended length of the DNA molecule is approximately equal to the position of the highest fluorescent signal, the desired extension direction of the DNA molecule is vertical with respect to the metal surface. It is desirable to narrow the position distribution when the DNA is extended. This can be accomplished by extension direction control techniques. In other words, the extension direction of the DNA molecule can be controlled by external forces, such as magnetic force, electrical force and/or buoyancy. FIGS. 8A-8E schematically illustrate some examples for regulating the DNA extension direction using various means for applying an external force.

Figure 8A:
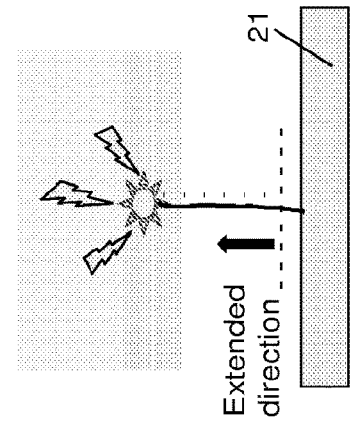
FIGS. 8A-8E schematically illustrate various methods of regulating the direction of extension of the DNA molecule immobilized on the metal film.

FIG. 8A shows magnetic regulation, where either the fluorescent dye has paramagnetism, or the DNA is modified with another molecule having paramagnetism at the free terminus (i.e. the terminus of the DNA not immobilized on the metal surface 21). An external magnetic field is applied to the sample.

Figure 8B:
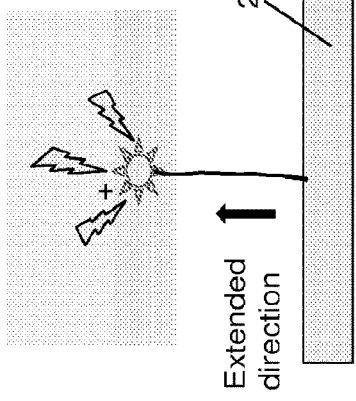
Figure 8C:
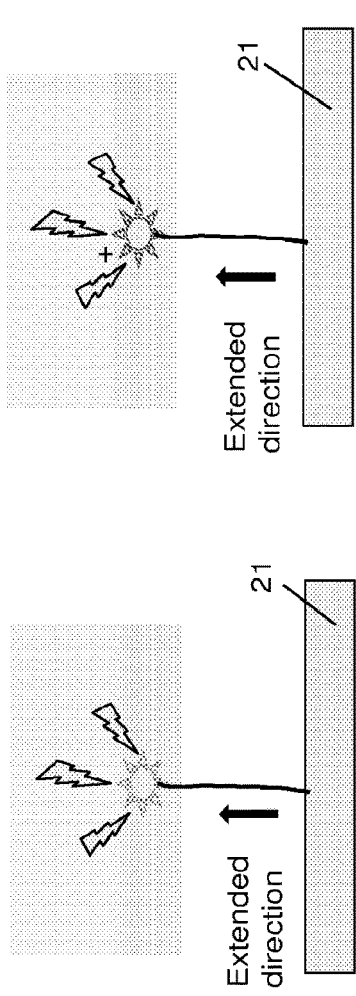

FIG. 8B shows electric regulation, where either the fluorescent dye has a positive (or negative) electric charge, or the DNA is modified with another molecule having a positive (or negative) electric charge at the free terminus. An external electric field of an appropriate direction is applied to the sample. FIG. 8C shows another example of electric regulation, where the DNA molecule has a negative charge (which is DNA's intrinsic charge), and the surface of the thin metal film is also negatively charged.

Figure 8D:
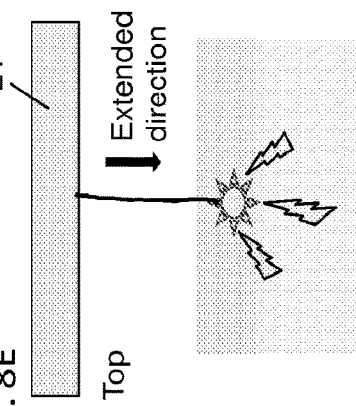
Figure 8E:
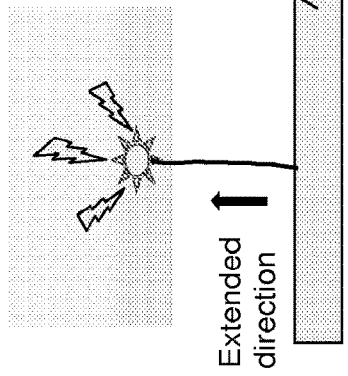

FIG. 8D shows buoyancy regulation, where the fluorescent dye has a lower density than the sample medium, or the DNA is modified with microbubbles at the free terminus to create buoyancy. Microbubbles can be made using known technology. The thin metal film is located below the sample medium and the DNA molecules extend upwardly. FIG. 8E shows another example of buoyancy regulation, where the fluorescent dye has a higher density than the sample medium. Here the thin metal film 21 is located above the sample medium, and the DNA molecules extend downwardly.

Since most of the molecules in the sample including the ligand have electric charges, and the densities of the sample medium tend to be different from patient to patient, electric and buoyancy regulations may be less reliable, and magnetic regulation is more suitable for this purpose.

It should be noted that in these examples of DNA extension direction control techniques, the external force (magnetic, electric, buoyancy) should be weaker than the force that maintains the DNA in the folded structure when the target is absent.

Another technique to increase signal to noise ratio is to attract fluorescent molecule to the metal surface to reduce the noise when the target is absent. To achieve this, the metal film surface can be modified so that it interacts with the fluorescent dye or the DNA terminus where the fluorescent dye is attached.

As discussed earlier, while a quenching module is not required to be attached near the immobilized terminus of the DNA molecule for quenching the fluorescence when the DNA is folded, having such a quenching module can be advantageous as it reduced noise and increases signal to noise ratio.

The methods described above can be applied to other DNA molecular switches whose structure is changed in the presence of an analyte (such as DNA, RNA, protein, metabolite, virus, cells, etc.).

It will be apparent to those skilled in the art that various modification and variations can be made in the SPFS biosensor and related method of the present invention without departing from the spirit or scope of the invention. Thus, it is intended that the present invention cover modifications and variations that come within the scope of the appended claims and their equivalents.

What is claimed is:
1. An optical biosensor comprising:
   a prism;
   a thin metal film formed on the prism, being configured to generate an electrical field near its surface when an incident light of a predetermined wavelength is irradiated on the prism at a predetermined angle, the electrical field forming a fluorescent quenching region located between 0-5 nm from the surface of the metal film and a fluorescent enhancing region located farther away from the surface than the fluorescent quenching region;
   a nucleic acid molecule having one end immobilized on the surface of the metal film and having another end modified with a fluorescent marker, wherein the nucleic acid molecule is configured to change its structure either from a folded state to an extended state upon binding to a target, or from an extended state to a folded state upon binding to a target,
   wherein the nucleic acid molecule is configured such that when it is in the extended state, the fluorescent marker is located in the fluorescent enhancing region and emits a first fluorescent signal, and when the nucleic acid molecule is in the folded state, the fluorescent marker is located in the fluorescent quenching region and emits no fluorescent signal or a second fluorescent signal which is weaker than the first fluorescent signal; and
   a magnet for applying an external magnetic force on the fluorescent marker or the nucleic acid molecule to urge the nucleic acid molecule to extend in a direction away from the surface of the metal film, wherein either the fluorescent marker has paramagnetism, or the nucleic acid molecule is modified with another molecule having paramagnetism at the end which is modified with the fluorescent marker.

2. The optical biosensor of claim 1, wherein the biosensor is a surface plasmon field-enhanced fluorescence spectroscopic sensor.

3. A method of using the optical biosensor of claim 1, comprising:
   applying a sample to the surface of the metal film of the biosensor; and
   measuring fluorescent signals from the biosensor.

4. The method of claim 3, further comprising: applying the magnetic field on the fluorescent marker or the nucleic acid molecule to urge the nucleic acid molecule to extend in a direction away from the surface of the metal film.

* * * * *